United States Patent [19]
Miyasaka et al.

[11] 4,399,276
[45] Aug. 16, 1983

[54] 7-SUBSTITUTED CAMPTOTHECIN DERIVATIVES

[75] Inventors: Tadashi Miyasaka, Yokohama; Masahiko Mutai, Higashiyamato; Seigo Sawada, Tokyo; Kenichiro Nokata, Mitaka, all of Japan

[73] Assignee: Kabushiki Kaisha Yakult Honsha, Tokyo, Japan

[21] Appl. No.: 336,494

[22] Filed: Dec. 31, 1981

[30] Foreign Application Priority Data

Jan. 9, 1981 [JP] Japan ................................ 56-1148
Jan. 9, 1981 [JP] Japan ................................ 56-1149
May 7, 1981 [JP] Japan ................................ 56-67594

[51] Int. Cl.³ .......................................... C07D 491/22
[52] U.S. Cl. ................................. 542/416; 542/417; 542/418; 542/420; 546/48
[58] Field of Search .............. 542/417, 418, 420, 416; 546/48

[56] References Cited

FOREIGN PATENT DOCUMENTS 3026172 2/1981 Fed. Rep. of Germany .

Primary Examiner—John M. Ford
Assistant Examiner—Bernard Dentz
Attorney, Agent, or Firm—Birch, Stewart, Kolasch & Birch

[57] ABSTRACT

New 7-substituted camptothecin derivatives possessing anti-tumor activity with slight toxicity, represented by the general formula:

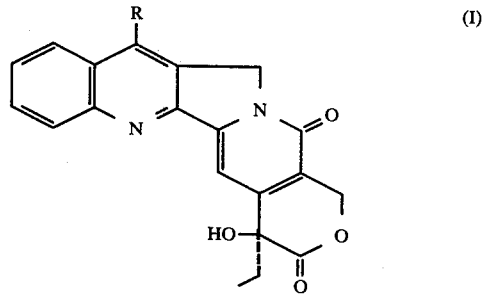

(I)

wherein R stands for —CHO, —CH$_2$OR', —CH(OR')$_2$ or —CH=N—X where R' is a lower alkyl group with 1–6 carbon atoms or a phenylalkyl group with 1–3 carbon atoms in the alkylene moiety thereof, and X is a hydroxyl group or —NR$^1$R$^2$ where R$^1$ and R$^2$ are the same or different and each represents a hydrogen atom or a lower alkyl group with 1–6 carbon atoms, or when R$^1$ is hydrogen, R$^2$ may be a lower alkyl group with 1–6 carbon atoms, a substituted or unsubstituted aryl group, a carbamoyl group, an acyl group, an aminoalkyl group or an amidino group, or when R$^1$ is the lower alkyl group, R$^2$ may be an aminoalkyl group, or R$^1$ and R$^2$ may be combined together with the nitrogen atom, to which R$^1$ and R$^2$ are bound, to form a heterocyclic group, and quaternary salts thereof. These 7-substituted camptothecin derivatives are prepared by treating 7-hydroxymethyl- or 7-dialkoxymethyl-camptothecin with a catinoid reagent, or treating 7-formyl- or 7-hydroxymethyl-camptothecin with an acid in the presence of a lower alkanol or phenylalkanol, or treating 7-formylcamptothecin or an acetal thereof with a nitrogen-containing carbonyl reagent and optionally treating the resulting product with a quaternating agent.

22 Claims, No Drawings

7-SUBSTITUTED CAMPTOTHECIN DERIVATIVES

BACKGROUND OF THE INVENTION

1. Field of the Invention

This invention relates to new camptothecin derivatives possessing anti-tumor activity (including carcinostatic activity) and to processes for the preparation of such derivatives. More particularly, this invention relates to new camptothecin derivatives carrying an aldehyde group or a functionally modified aldehyde group in the 7-position thereof and possessing anti-tumor activity with a low level of toxicity as well as processes for the preparation of such new camptothecin derivatives.

2. Description of the Prior Art

Camptothecin is a cytotoxic alkaloid isolated from leaves and barks of Camptotheca accuminata (Nyssaceae), a plant native to China, which has a pentacyclic structure consisting of a characteristic fused 5-ring system of quinoline (rings A and B), pyrroline (ring C), α-pyridone (ring D) and a six-membered lactone (ring E) and is distinguished by displaying a strong inhibitory activity toward biosynthesis of nucleic acid. In addition, camptothecin is a unique anti-tumor substance characterized by its rapid and reversible action and its lack of any cross-tolerance with the existing anti-tumor agents and by exhibiting a strong anti-tumor activity against experimentally transplanted carcinoma such as leukemia L-1210 in mice or Walker 256 tumor in rats. Although camptothecin is still regarded as one of the most potent substances possessing anti-tumor activity, the use of this compound itself for clinical treatments is significantly limited because of high toxicity.

Accordingly, a number of attempts have been made to reduce the toxicity of camptothecin while maintaining its anti-tumor activity by converting camptothecin chemically into its derivatives. The chemical modifications so far reported are mainly about the rings D and/or E of camptothecin, but the results of such modifications revealed only failure in maintaining expected anti-tumor activity and poor improvement in toxicity [J. Med. Chem., 19 (1976), 675]. From the chemotherapeutic point of view, therefore, it is of importance that the chemical modifications of camptothecin should be restricted in the rings A, B and C without effecting any change in the rings D and E which are conceivable to be one of the essential structural elements for the expression of the above mentioned characteristic biological activities.

Except for a method for functionalizing the 12-position of camptothecin reported in 1976 which comprises a series of troublesome conversion and purification operations starting with nitration at the 12-position [P. Pei-chuang et al., Hau Hsueh Pao 33 (1975); Chem. Abstr. 84 (1976) 115629p], however, no success was reported until 1979 in connection with chemical functionalization of camptothecin in a moiety involving the rings A, B and C. This is probably ascribable to the reasons that camptothecin itself is only sparingly soluble in various organic solvents and that camptothecin possessing the nature of heterocyclic rings in its molecule is resistant to the so-called electrophilic reactions conventionally carried out on aromatic rings. In the present status, such obstacles strongly discourage chemical modifications of camptothecin contemplated academically for preparing new classes of derivatives thereof.

Under the above mentioned circumstances, the present inventors previously found together with co-workers a process for introducing a hydroxymethyl group into the 7-position of camptothecin efficiently in a single step and prepared a number of new camptothecin derivatives possessing anti-tumor activity with slight toxicity from 7-hydroxymethylcamptothecin obtained according to the above process (Japanese Laid-open Patent Applns. Nos. Sho. 56-12391, 56-12392, 56-12393 and 56-12394; U.S. Ser. No. 166,953; DOS No. 30 26 172). However, the kinds of camptothecin derivatives prepared according to these processes are still limited.

For further researches on the relation between the substituents in camptothecin derivatives and anti-tumor activity and/or toxicity, therefore, there is still a great demand in this art for developing further new classes of camptothecin derivatives possessing a low level of toxicity while maintaining the inherent anti-tumor activity by chemically modifying 7-hydroxymethylcamptothecin in a single step without destroying the structure of the rings D and E in the camptothecin molecule.

BRIEF SUMMARY OF THE INVENTION

Accordingly, it is an object of the present invention to provide new 7-substituted camptothecin derivatives.

It is another object of the present invention to provide new 7-substituted camptothecin derivatives which are strong in anti-tumor activity and possess good absorbability in the living body with very low toxicity.

It is still another object of the present invention to provide processes for the preparation of such new 7-substituted camptothecin derivatives.

It is further a object of the present invention to provide new means for converting the 7-hydroxymethyl group in camptothecin into the 7-formyl group or its acetal group.

Other objects, features and advantages of the present invention will become apparent more fully from the following description.

DETAILED DESCRIPTION OF THE INVENTION

With a view to preparing new 7-substituted camptothecin derivatives possessing the inherent anti-tumor activity with extremely reduced toxicity, the present inventors have made further researches for chemically modifying the hydroxymethyl group existing in the 7-position of camptothecin, paying careful attention to the chemical modifications lest any destruction should occur in the structure of the rings D and E. As a result of such further researches, it has been found surprisingly that the 7-hydroxymethyl, 7-alkoxymethyl or 7-dialkoxymethyl group in camptothecin can be converted into a 7-formyl(aldehyde) group in a single step without attacking the rings D and E and the 7-formyl group in the resultant camptothecin derivative can be used for the preparation of various functionally converted aldehyde derivatives according to the methods known per se. The present invention has been accomplished on the basis of the above finding.

In accordance with the present invention, there are provided new 7-substituted camptothecin derivatives of the general formula:

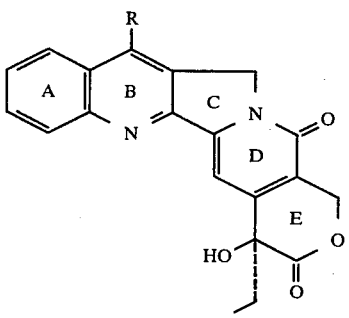

(I)

where R stands for —CHO, —CH$_2$OH', —CH(OR')$_2$ or —CH=N—X where R' is a lower alkyl group with 1-6 carbon atoms or a phenylalkyl group with 1-3 carbon atoms in the alkylene moiety thereof, and X is a hydroxyl group or —NR$^1$R$^2$ where R$^1$ and R$^2$ are the same or different and each represent a hydrogen atom or a lower alkyl group with 1-6 carbon atoms, or when R$^1$ is hydrogen, R$^2$ may be a lower alkyl group with 1-6 carbon atoms, a substituted or unsubstituted aryl group, a carbamoyl group, an acyl group, an aminoalkyl group or an amidino group, or when R$^1$ is the lower alkyl group, R$^2$ may be an aminoalkyl group, or R$^1$ and R$^2$ may be combined together with the nitrogen atom, to which R$^1$ and R$^2$ are bound, to form a heterocyclic group, as well as acid-addition and quaternary salts thereof.

When R', R$^1$ and/or R$^2$ represents a lower alkyl group with 1-6 carbon atoms, this group may be linear or branched. Typical examples of the lower alkyl group include methyl, ethyl, n-propyl, isopropyl, n-butyl, iso-butyl, sec.-butyl, tert-butyl, n-pentyl, iso-pentyl, n-hexyl and 2-methylpentyl groups. In view of the availability of alkanols as alkylating reactants, preferable lower alkyl groups are methyl, ethyl, n-propyl, isopropyl and n-butyl groups. The alkylene group of the phenylalkyl group has 1-3 carbon atoms and may be linear or branched. Preferable phenylalkyl groups are benzyl and phenethyl groups. A preferable aryl group is the phenyl group which may be substituted by one or more nitro groups, lower alkyl groups and halogen atoms. The amino-alkyl group preferably has 1-6 carbon atoms and may be linear or branched. The acyl group is preferably a residue of aliphatic carboxylic acids with 1-6 carbon atoms or benzoic acid which may be substituted by a lower alkyl group, alkoxy group, nitro group and/or halogen atoms. When R$^1$ and R$^2$ each stands for the lower alkyl group, these groups may be combined together to form an alkylene group and may form a 5-membered or 6-membered heterocyclic group together with the nitrogen atom to which the lower alkyl groups are bound. The alkylene group may be interrupted by one or two hetero atoms such as nitrogen, oxygen and sulfur atoms.

The new 7-substituted camptothecin derivatives of this invention possess anti-tumor activity with slight toxicity. Illustrative of the typical 7-substituted camptothecin derivatives of the present invention are 7-methoxymethylcamptothecim, 7-ethoxymethylcamptothecin, 7-propoxyethylcamptothecin, 7-butoxymethylcamptothecin, 7-dimethoxymethylcamptothecin, 7-diethoxymethylcamptothecin, 7-dipropoxymethylcamptothecin, 7-dibutoxymethylcamptothecin, camptothecin-7-aldehyde, camptothecin-7-aldehyde oxime, camptothecin-7-aldehyde hydrazone, camptothecin-7-aldehyde methylhdrazone, camptothecin-7-aldehyde phenylhydrazone, camptothecin-7-aldehyde 2,4-dinitrophenylhydrazone, camptothecin-7-aldehyde thiosemicarbazone, camptothecin-7-aldehyde semicarbazone, camptothecin-7-aldehyde hdrazone with 1-amino-4-methylpiperazine, camptothecin-7-aldehyde hydrazone with pyridinium acetohydrazide, camptothecin-7-aldehyde hydrazone with dimethylaminoacetohydrazide, camptothecin-7-aldehyde phenylsemicarbazone and camptothecin-7-aldehyde hydrazone with 1-aminooxazoline.

The 7-substituted camptothecin derivatives of the general formula (I) wherein R stands for the grouping —CH=N—X where X is especially an amino group —NR$^1$R$^2$ form acid-addition and quaternary salts thereof with an acid such as hydrochloric acid or an alkyl halide such as methyl or ethyl bromide. These quaternary salts including acid-addition salts are of course involved in the scope of the present invention.

In accordance with the present invention, there is also provided a process for the preparation of the new 7-substituted camptothecin derivatives of the general formula (I).

In one embodiment of the process, camptothecin-7-aldehyde of the formula:

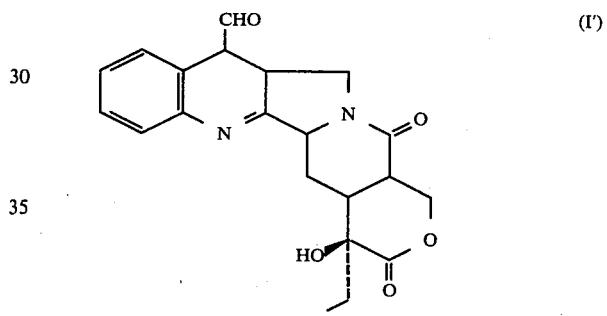

(I')

is prepared in a single step by treating 7-hydroxymethylcamptothecin with a cationoid reagent.

The cationoid reagent used in this reaction includes a variety of mineral (or inorganic) acids and organic acids, Lewis acids, organic acid halides and halogenating agents. Examples of the mineral or inorganic acid include sulfuric acid, hydrochloric acid, hydrobromic acid, perchloric acid and hydroiodic acid. Such acid is preferably used as a 20-50% aqueous solution to which 7-hydroxymethylcaptothecin is added. A solution of the 7-hydroxymethylcamptothecin thus formed is then boiled under reflux for a given period of time. Examples of the organic acids include carboxylic acid such as acetic acid, propionic acid, chloroacetic acid, benzoic acid and trifluoroacetic acid and sulfonic acids such as p-toluenesulfonic acid, methanesulfonic acid and ethanesulfonic acid. These cationoid agents are preferably used in a solvent, for example, a polar solvent such as water, dimethylformamide, alcohols, dimethylsulfoxide, dioxane or tetrahydrofuran. In case acetic acid or the like organic acid is used as the cationoid agent, such organic acid also functions as a solvent so that the reaction can be carried out without using any solvent. Examples of Lewis acids utilizable as another type of the cationoid reagent include boron trifluoride etherate, aluminum chloride, ferric chloride and stannic chloride. In this case, a Lewis acid is used in a 5-10 molar amount in an aprotic solvent such as nitrobenzene, dioxane, tetrachloroethane or diglyme, and the reaction is preferably conducted at 90°–100° C. Examples of organic acid halides utilizable as still another type of the cationoid reagent include p-toluensulfonyl chloride and phenylacetyl chloride. In this case, the organic acid chloride is used preferably in a 5–10 molar amount in a polar solvent such as dimethylformamide, dimethylsulfoxide, dioxane or pyridine, and the reaction is preferably carried out at 90°–100° C. Halogenating agents, for example, reagents usually employed for chlorination such as phosphorus oxychloride, thionyl chloride, phosphorus trichloride or triphenylphosphine-carbon tetrachloride can also be used as the cationoid reagent. In this case, such halogenating agent is preferably used in a 5–10 molar amount in a solvent such as pyridine or dioxane, and the reaction is carried out preferably, at about 100° C.

After completion of the reaction, the solvent used is removed by evaporation under reduced pressure and the residue is subjected to column chromatography on silica gel in a usual manner. Chloroform alone or a solvent mixture containing chloroform as a predominant ingredient is used for this chromatographic purification treatment.

According to this embodiment, the hydroxymethyl group of 7-hydroxymethylcamptothecin can be converted into the formyl group in a single step without using any oxidizing agent. Such oxidizing method is indeed novel and has not been known hitherto even in the treatment of ordinary primary alcohols or heterocyclic compounds such as hydroxymethylquinoline.

7-Hydroxymethylcamptothecin utilized as starting material in this embodiment can be prepared easily in one step from the naturally occurring (+)-camptothecine or the corresponding (−)- and dl-camptothecins synthetically obtained, according to the process disclosed in Japanese Laid-open Patent Appln. No. 56-12391 (U.S. Ser. No. 166,953; DOS 30 26 172).

Camptothecin-7-aldehyde(7-formylcamptothecin) thus prepared is effective as an anti-tumor agent with reduced toxicity but is also useful as an intermediate product for the preparation of various new 7-substituted camptothecin derivatives utilizable as anti-tumor agents which are lower in toxicity than camptothecin itself.

According to one route for further modifying the camptothecin-7-aldehyde, an ordinary acetalization treatment can be applied to this product to obtain a 7-dialkoxymethylcamptothecine and carried out by heating comptothecin-7-aldehyde in an excess amount of R'OH in the presence of an acid in a usual manner.

According to another route for further modifying the camptothecin-7-aldehyde, an active amino compound known as a nitrogen-containing carbonyl reagent can be used in a usual manner for chemically modifying the carbonyl function of camptothecin-7-aldehyde. More precisely, various new 7-substituted camptothecin derivatives of the general formula:

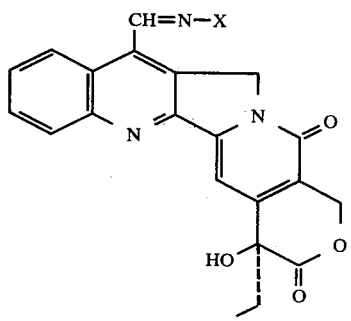

wherein X has the same meaning as given above, as well as quaternary salts thereof, are prepared by reacting camptothecin-7-aldehyde or an acetal thereof with an active amino compound of the general formula:

$$H_2N-X \qquad (II)$$

wherein X has the same meaning as given above, in the manner known per se and optionally treating the resultant product with a quaternating agent.

Examples of the active amino compound of the general formula (II) include hydroxylamine; hydrazine derivatives such as hydrazine itself, methylhydrazine, ethylhydrazine, phenylhydrazine, p-nitrophenylhydrazine, 2,4-dinitrophenylhydrazine and p-toluenesulfonylhydrazine, N-aminoguanidine, 1-amino-4-methylpiperazine; Girard reagents such as N,N-dimethylglycinhydrazide hydrochloride, trimethylammonium acetohydrazide chloride, pyridinium acetohydrazide chloride and N-aminohydantoin; isonicotinic acid hydrazide; semicarbazide derivatives such as semicarbazide, phenylsemicarbazide and thiosemicarbazide; and semioxazoline. Camptothecin-7-aldehyde is reacted according to the method known per se with the active amino compound preferably in an appropriate solvent such as methanol, ethanol, pyridine, acetic acid or a mixture of ethanol and pyridine at a temperature ranging from room temperature to 80° C. If the active amino compound is in the form of a salt such as the hydrochloride or sulfate, the reaction will be conducted in pyridine or together with a base such as sodium acetate, triethylamine or pyridine in an amount equivalent to the acid contained in the salt so that the active amino compound may be reacted in the free form with camptothecin-7-aldehyde. In the reaction of camptothecin-7-aldehyde with hydroxylamine, camptothecin-7-aldoxime in the E-form and Z-form are obtained almost in a ratio of 1:1. Camptothecin-7-aldehyde hydrazones obtained by the reaction with 1-amino-4-methylpiperazine or a Girard reagent can be dissolved in water by quaternating their

moiety with a quaternating agent such as hydrochloric acid or the like inorganic acid or an alkyl halide.

A variety of new 7-substituted camptothecin derivatives of the general formula (I″) are also useful as antitumor agents with low toxicity.

In another embodiment of the process of this invention 7-alkoxymethyl- and 7-dialkoxymethylcamptothecins of the general formulas:

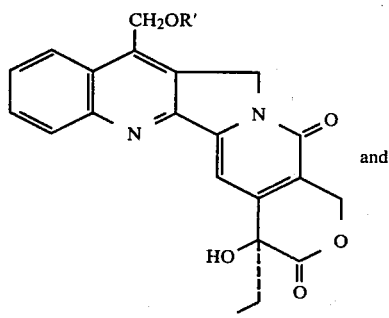
(I'''-A)

and

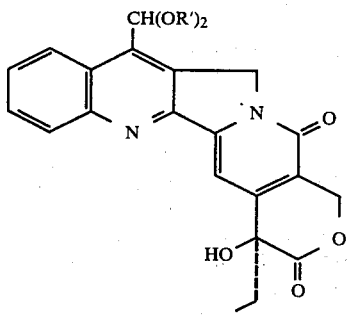
(I'''-B)

wherein R' has the same meaning as given above, are prepared in a single step by treating 7-hydroxymethylcamptothecin with an acid in the presence of a lower alkanol or phenylalkanol of the general formula:

R'—OH  (III)

wherein R' has the same meaning as given above.

The lower alkanols of the general formula (III) include, for example, methanol, ethanol, propanol, isopropanol, n-butanol, isobutanol, tert-butanol, n-amyl alcohol, isoamyl alcohol, tert-amyl alcohol, n-hexanol and 2-ethylbutanol. Illustrative of the phenylalkanols are, for example, benzyl alcohol, phenethyl alcohol and phenylpropanol. Examples of the acid utilizable for this reaction include mineral acids such as sulfuric acid, hydrochloric acid, hydrobromic acid and perchloric acid; Lewis acids such as boron trifluoride, aluminum chloride, ferric chloride and stannic chloride; strong organic carboxylic acids such as trifluoroacetic acid and trichloroacetic acid; and organic sulfonic acids such as benzenesulfonic acid, p-toluenesulfonic acid, methanesulfonic acid and ethanesulfonic acid.

The above reaction is preferably carried out by maintaining 7-hydroxymethylcamptothecin in a lower alkanol or phenylalkanol of the general formula (III) as a solvent in the presence of the above mentioned acid at a temperature from room temperature to the reflux temperature. When the acid is used in a catalytic amount or several molar equivalent amount, a 7-dialkoxymethylcamptothecin is obtained exclusively or preferentially. On the other hand, when the acid is used in a large excess amount, e.g. in a 150–250 molar equivalent amount, a 7-alkoxymethylcamptothecin is obtained exclusively or preferentially. In the event that both of a 7-dialkoxymethylcamptothecin and a 7-alkoxymethylcamptothecin are formed concurrently, both products can be separated and purified by subjecting the reaction product to column chromatography on silica gel or high speed fluid chromatography. The 7-dialkoxymethylcamptothecin thus obtained has a structure corresponding to an acetal of camptothecin-7-aldehyde which, as described previously with respect to a further modification of camptothecin-7-aldehyde, is obtainable in a high yield by heating the 7-aldehyde in an excess amount of a lower alkanol in the presence of an acid under the conditions usually employed for acetalization.

On the other hand, the 7-dialkoxymethylcamptothecin can be converted theoretically into camptothecin-7-aldehyde according to the method known per se, for example, hydrolysis under acidic conditions.

According to this embodiment, 7-hydroxymethylcamptothecin can be converted with a cheap reagent into 7-alkoxymethylcamptothecins and 7-dialkoxymethylcamptothecins in a single step. It is indeed surprising that 7-hydroxymethylcamptothecin can be converted into a 7-dialkoxymethylcamptothecin which corresponds to an acetal of camptothecin-7-aldehyde without using any oxidizing agent. Such method is indeed novel, as in the firstly mentioned embodiment, and has not been known hitherto even in the treatment of ordinary primary alcohols or heterocyclic compounds such as hydroxymethylquinoline.

The present invention is of particular significance in developing a number of new camptothecin derivatives useful as anti-tumor agents possessing anti-tumor activity with slight toxicity and as intermediate products for preparing other useful products as well as processes for preparing these new derivatives in a simple operation.

The present invention will now be illustrated in more detail by way of examples. In these examples, the temperature is shown by centigrade (°C.) and the relation between part and percentage is by weight unless otherwise indicated.

EXAMPLE 1

7-Hydroxymethylcamptothecin (200 mg, 0.529 mmol) was suspended in water (20 ml) and conc. sulfuric acid (6 ml) in small portions was added thereto to make the whole to a solution. The solution was boiled under reflux for 30.5 hours. The reaction mixture was, after being allowed to stand for cooling, diluted with ice water (500 ml) and extracted with CHCl$_3$ (300 ml×3). A solid substance insoluble in both of the aqueous phase and the CHCl$_3$ phase was collected by filtration and dried (recovery of 7-hydroxymethylcamptothecin). The CHCl$_3$ layers were combined, dried over MgSO$_4$, filtered and concentrated until dryness under reduced pressure. The residue was purified by way of column chromatography (CHCl$_3$) on silica gel whereupon 39 mg (yield: 29.7%) of camptothecin-7-aldehyde was obtained. 7-Hydroxymethylcamptothecin recovered was 68 mg in total. Analytical data of the camptothecin-7-aldehyde were as shown below.

Yellow prismatic crystals M.P. 256°–260° (dec) (from benzene)

IR$\nu_{max}^{KBr}$ cm$^{-1}$: 3350, 3080, 2960, 2925, 2860, 1750 (lactone), 1960 (CHO), 1655 (lactam), 1600, 1460, 1225, 1155, 765

NMR (CDCl$_3$)$\delta$: 1.18 (3H, t, J=7.5 Hz), 1.93 (2H, q, J=7.5 Hz), 5.31 (1H, d, J=16 Hz, C$_{17}$-H), 5.63 (2H, s, C$_5$-H), 5.80 (1H, d, 16 Hz, C$_{17}$-H), 7.68 (1H, s, C$_{14}$-H), 7.90 (2H, m), 8.38 (1H, m), 8.80 (1H, m, C$_9$-H), 11.20 (1H, s, CHO).

MS:m/e 376[M+] (C$_{21}$H$_{16}$N$_2$O$_5$=376)

EXAMPLE 2

7-Hydroxymethylcamptothecin (200 mg, 0.529 m-mol) was dissolved in acetic acid (100 ml) and the solution was boiled under reflux for 5.5 hours. The reaction mixture was concentrated until dryness under reduced pressure and the residue was subjected to separation and purification by way of column chromatography (CHCl$_3$) on silica gel (30 g) whereby 7-acetoxymethylcamptothecin (19 mg, yield: 8.5%) and camptothecin-7-aldehyde (135 mg, yield: 67.8%) were obtained.

EXAMPLE 3

7-Hydroxymethylcamptothecin (100 mg, 0.264 m-mol) was suspended in tetrachloroethane-dioxane (30 ml-20 ml). Boron trifluoride-ether (500 $\mu$l, about 3.96 m-mol) was added to the suspension and the whole was boiled under reflux for 14.5 hours. The reaction mixture was concentrated until dryness under reduced pressure and the residue was suspended in water (100 ml) and extracted with chloroform (100 ml×3). The chloroform layers were combined, dried over magnesium sulfate, filtered and concentrated until dryness under reduced pressure. The residue was purified by way of column chromatography (chloroform) on silica gel whereupon 26 mg (yield: 26.1%) of camptothecin-7-aldehyde was obtained as yellow crystals.

EXAMPLE 4

7-Hydroxycamptothecin (378 mg, 1 m-mol) was dissolved in pyridine (200 ml) while warm. p-Toluenesulfonyl chloride (950 mg, 5 m-mol) was added to the solution and the mixture was stirred for 4.5 hours at 80°–90° C. The reaction mixture was concentrated until dryness under reduced pressure and the residue was subjected to separation and purification by way of column chromatography (CHCl$_3$) on silica gel whereby 255 mg (yield: 68.7%) of camptothecin-7-aldehyde was obtained as a yellow solid.

EXAMPLE 5

7-Hydroxymethylcamptothecin (100 mg, 0.264 m-mol) was dissolved in pyridine (50 ml) and dimethylformamide (50 ml). Phenylacetyl chloride (200 mg, 1.29 m-mol) was added to the solution and the mixture was stirred for 6 hours at 90°–100° C. The reaction mixture was concentrated until dryness under reduced pressure and the residue was subjected to separation and purification by way of column chromatography (CHCl$_3$) on silica gel whereby 7-phenylacetoxymethylcamptothecin (74 mg, yield: 56.5%) and camptothecin-7-aldehyde (19 mg, yield: 19.1%) were obtained.

EXAMPLE 6

7-Hydroxymethylcamptothecin (100 mg, 0.268 m-mol) was suspended in dioxane-chloroform (15 ml-7 ml). Phosphorus oxychloride (0.5 ml, 5.37 m-mol) was added to the suspension and the mixture was boiled under reflux for 2 hours. The reaction mixture was concentrated until dryness under reduced pressure and the residue was subjected to separation and purification by way of column chromatography (CHCl$_3$) on silica gel whereby 34 mg (yield: 34.2%) of camptothecin-7-aldehyde was obtained as a yellow solid.

EXAMPLE 7

7-Hydroxymethycamptothecin (100 mg, 0.264 m-mol) was suspended in dioxane-chloroform (75 ml-25 ml). Thionyl chloride (680 mg, 5.71 m-mol) was added to the suspension and the mixture was boiled under reflux for 14 hours. The reaction mixture was concentrated until dryness under reduced pressure and the residue was purified by way of column chromatography (chloroform) on silica gel whereby 57 mg (yield: 57.2%) of camptothecin-7-aldehyde was obtained as a yellow solid.

EXAMPLE 8

7-Hydroxymethylcamptothecin (200 mg, 0.529 m-mol) was dissolved in dimethylformamide (150 ml) while warm. Triphenylphosphine (700 mg, 2.67 m-mol) and carbon tetrachloride (300 $\mu$l, ca. 3.11 m-mol) were added to the solution and the mixture was stirred for 10 hours at 95°–100° C. The reaction mixture was concentrated until dryness under reduced pressure and the residue was subjected to separation and purification whereby 101 mg (yield: 56.4%) of camptothecin-7-aldehyde was obtained as a yellow solid. A small amount (about 20 mg) of 7-hydroxymethylcamptothecin was recovered.

EXAMPLE 9

7-Hydroxymethylcamptothecin (100 mg, 0.264 m-mol) was suspended in methanol-dioxane (20 ml-20 ml) and conc. sulfuric acid (3 ml) was added to the suspension to form a solution. The mixture was boiled under reflux for 35 hours and then concentrated until dryness under reduced pressure. The residue was leached with H$_2$O (100 ml) and then extracted with CHCl$_3$ (100 ml×3). The CHCl$_3$ phase was dried with MgSO$_4$, filtered and concentrated until dryness under reduced pressure. The residue was subjected to separation and purification by way of column chromatography (CHCl$_3$) on silica gel whereby 7-dimethoxymethylcamptothecin (19 mg, yield: 17.0%) and 7-methoxymethylcamptothecin (40 mg, yield: 38.6%) were obtained.

Analytical data of these products are as follows:

(1) 7-methoxymethylcamptothecin
light yellowish white needle crystals
M.P. 252°–257° (dec.) (methanol-chloroform)
IR$\nu_{max}^{KBr}$ cm$^{-1}$: 3350, 2920, 1755, 1655, 1600, 1115, 760
NMR(DMSO-d$_6$)$\delta$: 0.94 (3H, t, J=7 Hz), 1.88 (2H, q, J=7 Hz), 3.31 (3H, s), 5.20 (2H, s), 5.36 (2H, s), 5.46 (2H, s), 6.51 (1H, s, D$_2$O exchangeable), 7.39 (1H, s), 7.60–8.30 (4H, m)
MS: m/e 392[M+] (C$_{22}$H$_{20}$N$_2$O$_5$=392)

(2) 7-dimethoxymethylcamptothecin
light yellowish white needle crystals
M.P. 222°–224° (dec.) (n-hexane-chloroform)
IR$\nu_{max}^{KBr}$ cm$^{-1}$: 3340, 2950, 2920, 1750, 1655, 1440, 1155, 1050, 750
NMR(CDCl$_3$)$\delta$: 1.05 (3H, t, J=7 Hz), 1.90 (2H, q, J=7 Hz), 3.40 (3H, s), 3.41 (3H, s), 5.29 (1H, d, J=16 Hz), 5.49 (2H, s), 5.77 (1H, d, J=16 Hz), 6.25 (1H, s), 7.67 (1H, s), 7.67–8.34 (4H, m)
MS: m/e 422[M+] (C$_{23}$H$_{22}$N$_2$O$_6$=422)

EXAMPLE 10

7-Hydroxymethylcamptothecin (200 ml, 0.529 m-mol) was suspended in ethanol (20 ml) and conc. sulfuric acid (6 ml) was added to the suspension to form a solution. The solution was boiled under reflux for 7 hours and the reaction mixture was concentrated until dryness under reduced pressure. The residue was leached with H$_2$O (500 ml) and extracted with chloroform (200 ml×3). A solid insoluble to both of the aqueous phase and the chloroform phase was collected by filtration (recovery of 7-hydroxymethylcamptothecin). The chloroform layers were combined, dried over MgSO$_4$ and concentrated until dryness and the residue was purified by way of column chromatography (CHCl$_3$) on silica gel whereby 7-diethoxymethylcamptothecin (24 mg, yield: 16%) and 7-ethoxymethylcamptothecin (27 mg, yield: 20.7%) were obtained. A small amount of 7-hydroxymethylcamptothecin was also recovered (79 mg in total amounts recovered).

Analytical data:

(1) 7-ethoxymethylcamptothecin
Light yellowish white needle crystals
M.P. 139°–142° (ethanol-chloroform)
IR$\nu_{max}^{KBr}$ cm$^{-1}$: 3400, 2950, 2920, 2860, 1745, 1655, 1600, 1230, 1155, 760
NMR (CDCl$_3$)δ: 1.04 (3H, t, J=7.3 Hz), 1.38 (3H, t, J=6.8 Hz), 1.83 (2H, q, J=7.3 Hz), 3.81 (2H, q, J=6.8 Hz), 5.18 (2H, s), 5.27 (1H, d, J=16.6 Hz), 5.43 (2H, s), 5.76 (1H, d, J=16.6 Hz), 7.65 (1H, s), 7.65–8.28 (4H, m)
MS: m/e 406[M+] (C$_{23}$H$_{22}$N$_2$O$_5$=406)

(2) 7-diethoxymethylcamptothecin
Light yellowish white needle crystals
M.P. 223°–224° (dec.) (ethanol)
IR$\nu_{max}^{KBr}$ cm$^{-1}$: 3400, 2960, 2920, 2880, 1740, 1655, 1600, 1155, 1050, 765
NMR (CDCl$_3$)δ: 1.17 (3H, t, J=7.3 Hz), 1.26 (3H, t, J=6.8 Hz), 1.28 (3H, t, J=6.8 Hz), 1.90 (2H, q, J=7.3 Hz), 3.70 (4H, m), 5.29 (1H, d, J=16 Hz), 5.50 (2H, s), 5.76 (1H, d, J=16 Hz), 6.36 (1H, s), 7.66 (1H, s), 7.64–6.87 (2H, m), 8.19–8.39 (2H, m)
MS: m/e 450[M+] (C$_{25}$H$_{26}$N$_2$O$_6$=450)

EXAMPLE 11

Camptothecin-7-aldehyde (200 mg, 0.532 m-mol) was dissolved in ethanol (50 ml). Boron trifluoride-ether (1 ml) was added to the solution and the mixture was boiled under reflux for 3.5 hours. The reaction mixture was concentrated until dryness under reduced pressure and the residue was shaken with water (100 ml) and chloroform (100 ml). The aqueous phase was further extracted with chloroform (100 ml). The chloroform layers were combined, dried over magnesium sulfate, filtered and concentrated until dryness under reduced pressure. The residue was purified by way of column chromatography (10% n-hexane-chloroform) on silica gel whereby 209 mg (yield: 87.3%) of 7-diethoxymethylcamptothecin was obtained as yellowish white crystals.

EXAMPLE 12

7-Hydroxymethylcamptothecin (100 mg, 0.264 m-mol) was suspended in n-butanol (30 ml). Concentrated sulfuric acid (5 ml) was added to the suspension and the mixture was boiled under reflux for 2.5 hours. The reaction mixture was concentrated until dryness under reduced pressure and the residue was leached with water (100 ml) and extracted with chloroform (100 ml×3). The chloroform layers were combined, dried with MgSO$_4$, filtered and concentrated until dryness under reduced pressure. The residue was purified by way of column chromatography (CHCl$_3$) on silica gel whereby 7-butoxymethylcamptothecin (48 mg, yield: 41.8%) was obtained as light yellowish white crystals.

Analytical data:
M.P. 142°–144° (n-hexane-chloroform)
IR$\nu_{max}^{KBr}$ cm$^{-1}$: 3400, 2950, 2930, 2860, 1745, 1660, 1155, 760
NMR(CDCl$_3$)δ: 0.97 (3H, t, J=7 Hz), 10.3 (3H, t, J=6.3 Hz), 1.10–1.80 (4H, m), 1.90 (2H, q, J=7 Hz), 3.70 (2H, t, J=6.3 Hz), 5.17 (2H, s), 5.28 (1H, d, J=16 Hz), 5.42 (2H, s), 5.75 (1H, d, J=16 Hz), 7.66 (1H, s), 7.50–8.30 (4H, m)
MS: m/e 434[M+] (C$_{25}$H$_{26}$N$_2$O$_5$=434)

EXAMPLE 13

7-Hydroxymethylcamptothecin (50 mg, 0.132 m-mol) was suspended in n-butanol (40 ml). Concentrated sulfuric acid (2 drops) was added to the suspension and the mixture was boiled under reflux for 30 minutes. The reaction mixture was concentrated until dryness under reduced pressure and the residue was leached with water (100 ml) and extracted with chloroform (100 ml×3). The chloroform layers were combined, dried over MgSO$_4$, filtered and concentrated until dryness under reduced pressure. The residue was purified by way of column chromatography (CHCl$_3$) on silica gel whereby 26 mg (yield: 38.7%) of 7-dibutoxymethylcamptothecin was obtained as light yellowish white crystals. Analytical data of this product were as shown below.

M.P. 107°–111° (n-hexane-chloroform)
IR$\nu_{max}^{KBr}$ cm$^{-1}$: 3400, 2950, 2930, 2860, 1750, 1660, 1610, 1590, 1155, 1050, 765
NMR(CDCl$_3$)δ: 0.88 (6H, t, J=7 Hz), 1.11 (3H, t, J=7 Hz), 1.14–1.79 (8H, m), 1.90 (2H, q, J=7 Hz), 3.57 (4H, m), 5.29 (1H, d, J=16 Hz), 5.50 (2H, s), 5.77 (1H, d, J=16 Hz), 6.36 (1H, s), 7.68 (1H, s), 7.50–7.80 (2H, m), 8.20–8.40 (2H, m)
MS: m/e 506[M+] (C$_{29}$H$_{34}$N$_2$O$_6$=506)

EXAMPLE 14

Camptothecin-7-aldehyde (350 mg, 0.93 m-mol) was dissolved in a mixture of ethanol (70 ml) and pyridine (10 ml) while warm. Hydroxylamine hydrochloride (200 mg, 2.88 m-mol) was added to the solution and the mixture was refluxed for 30 minutes. After allowing the mixture to stand for cooling, the precipitated crystals were collected by filtration and dried under reduced pressure whereby 315 mg (yield: 36.5%) of camptothecin-7-aldehyde oxime was obtained. By concentrating the filtrate until dryness, an additional 17 mg (4.7%) of this product was obtained.

M.P. 255°–257° C. (dec.)
IR$\nu_{max}^{KBr}$ cm$^{-1}$: 3300, 2970, 1740, 1655, 1590, 1155, 1005, 763
NMR (DMSO-d$_6$)δ ppm: 0.90 (3H, t, J=7.5 Hz), 1.92 (2H, q, J=7.5 Hz), 5.34 (2H, s), 5.43 (2H, s), 7.63 (1H, s), 7.75–8.34 (4H, m), 9.26 (1H, s), 12.54 (1H, s)
MS: m/e 391[M+] (C$_{21}$H$_{17}$N$_3$O$_3$=391)

EXAMPLE 15

Camptothecin-7-aldehyde (150 mg, 0.399 m-mol) was dissolved in a mixture of ethanol (40 ml) and pyridine (3 ml) while warm. 80% Hydrazine hydrate (100 mg, 1.6 m-mol) was added to this solution and the mixture was refluxed for 15 minutes. After allowing the mixture to stand for cooling, precipitated crystals were collected by filtration and dried under reduced pressure whereby 110 mg (71.0%) of camptothecin-7-aldehyde hydrazone was obtained. By concentrating the filtrate until dryness, an additional 15 mg (9.7%) of this product was obtained.

M.P. 262°–265° C. (dec.)

IR$\nu_{max}^{KBr}$ cm$^{-1}$: 3400, 2980, 1755, 1655, 1590, 1160, 1045, 763

EXAMPLE 16

Camptothecin-7-aldehyde (50 mg, 0.133 m-mol) was dissolved in a mixture of ethanol (20 ml) and pyridine (1 ml) while warm. Methylhydrazine (100 mg, 2.17 m-mol) was added to the solution and the mixture was refluxed for 30 minutes. After concentrating the mixture until dryness under reduced pressure, the residue was washed with ethanol and the precipitated crystals were collected by filtration whereupon 40 mg (74.4%) of camptothecin-7-aldehyde methylhydrazone was obtained.

M.P. 203°–205° C. (dec.)

IR$\nu_{max}^{KBr}$ cm$^{-1}$: 3250, 2950, 1740, 1650, 1500, 1370, 1150, 1030, 760

NMR (CDCl$_3$-DMSO-d$_6$) δ ppm: 0.95 (3H, t, J=7 Hz), 1.88 (2H, q, J=7 Hz), 3.13 (3H, d, J=4 Hz), 5.35 (2H, s), 5.40 (2H, dxd, J=14 Hz), 6.25 (1H, bs), 7.43 (1H, s), 7.5–8.8 (4H, m), 10.15 (1H, bs)

MS: m/e 404[M+]

EXAMPLE 17

Camptothecin-7-aldehyde (40 mg, 0.106 m-mol) was dissolved in a mixture of ethanol (15 ml) and pyridine (1 ml) while warm. Phenylhydrazine hydrochloride (25 mg, 0.173 m-mol) and sodium acetate (15 mg, 0.208 m-mol) were added to the solution and the mixture was refluxed for 10 minutes. After allowing the mixture to stand for cooling, water (15 ml) was added thereto and the precipitated crystals were collected by filtration whereby 35 mg (70.9%) of camptothecin-7-aldehyde phenylhydrazone was obtained.

M.P. 205°–208° C. (dec.)

IR$\nu_{max}^{KBr}$ cm$^{-1}$: 3240, 1735, 1655, 1600, 1530, 1495, 1255, 1157, 750

NMR (CDCl$_3$-DMSO-d$_6$) δ ppm: 0.97 (3H, t, J=7 Hz), 1.90 (2H, q, J=7 Hz), 5.44 (2H, dxd, J=16 Hz), 5.48 (2H, s), 6.90 (1H, bs), 7.0–8.9 (9H, m), 7.48 (1H, s), 11.24 (1H, s)

MS: m/e 466 [M+]

EXAMPLE 18

Camptothecin-7-aldehyde (50 mg, 0.133 m-mol) was dissolved in a mixture of ethanol (15 ml) and pyridine (1 ml) while warm. Acetic acid (2 ml) and 2,4-dinitrophenylhydrazine (50 mg, 0.253 m-mol) were added to the solution and the mixture was refluxed for 30 minutes. After allowing the mixture to stand for cooling, the precipitated crystals were collected by filtration whereupon 60 mg (81.1%) of camptothecin-7-aldehyde 2,4-dinitrophenylhydrazone was obtained.

M.P. 262°–264° C. (dec.)

IR$\nu_{max}^{KBr}$ cm$^{-1}$: 3520, 3270, 2880, 1720, 1655, 1590, 1500, 1320, 1220, 1135, 825, 765

NMR (CDCl$_3$-DMSO-d$_6$) δ ppm: 0.97 (3H, t, J=7 Hz), 1.89 (2H, q, J=7 Hz), 5.43 (2H, dxd, J=16 Hz), 5.47 (2H, s), 7.46 (1H, s), 7.6–8.9 (7H, m), 9.86 (1H, s), 12.13 (1H, s)

MS: m/e 556 [M+]

EXAMPLE 19

Camptothecin-7-aldehyde (100 ml, 0.27 m-mol) was dissolved in a mixture of ethanol (40 ml) and pyridine (3 ml) under warming. 1-Amino-4-methylpiperazine dihydrochloride monohydrate (100 mg, 0.49 m-mol) was added to the solution and the mixture was refluxed for 30 minutes. After allowing the mixture to stand for cooling, the precipitated crystals were collected by filtration and dried under reduced pressure whereupon 120 mg (82.6%) of camptothecin-7-aldehyde 4-methylpiperazinohydrazone hydrochloride was obtained.

M.P. 250° C. (dec.)

IR$\nu_{max}^{KBr}$ cm$^{-1}$: 3400, 2950, 2650, 2580, 2450, 1743, 1655 1600, 1545, 1370, 1155, 970, 763

This hydrochloride was treated with a 15% aqueous solution of sodium carbonate and the precipitate was extracted with chloroform. The chloroform phase was dried over magnesium sulfate and concentrated until dryness whereby the free hydrazone was obtained quantitatively.

NMR (CDCl$_3$) δ ppm: 1.05 (3H, t, J=7 Hz), 1.89 (2H, q, J=7 Hz), 2.44 (3H, s), 2.72 (4H, t), 3.53 (4H, t), 5.41 (2H, s), 5.51 (2H, dxd, J=16 Hz), 7.62 (1H, s), 7.4–8.3 (5H, m)

MS: m/e 473 [M+]

EXAMPLE 20

Camptothecin-7-aldehyde (100 mg, 0.266 m-mol) was dissolved in a mixture of ethanol (40 ml) and pyridine (3 ml) while warm. Pyridinium acetohydrazide chloride (50 mg, 0.269 m-mol) was added to the solution and the mixture was refluxed for 30 minutes. After allowing the mixture to stand for cooling, the precipitated crystals were collected by filtration and dried under reduced pressure whereby 80 mg (55.1%) of a hydrazone of camptothecin-7-aldehyde with pyridinium acetohydrazide chloride was obtained.

M.P. 255° C. (dec.)

IR$\nu_{max}^{KBr}$ cm$^{-1}$: 3440, 3050, 2950, 1740sh, 1700, 1655, 1595, 1155, 765

EXAMPLE 21

Camptothecin-7-aldehyde (30 mg, 0.080 m-mol) was dissolved in a mixture of ethanol (10 ml) and pyridine (1 ml) while warm. Thiosemicarbazide (27 mg, 0.296 m-mol) was added to the solution and the mixture was refluxed for 3 hours. After concentrating the mixture until dryness under reduced pressure, the residue was washed with ethanol and the precipitated crystals were collected by filtration and dried under reduced pressure whereby 28 mg (78.3%) of camptothecin-7-aldehyde thiosemicarbazone was obtained.

M.P. 263° C. (dec.)

IR$\nu_{max}^{KBr}$ cm$^{-1}$: 3250, 3180, 2970, 1740, 1650, 1590, 1395, 1280, 1155, 830, 760

NMR (DMSO-d$_6$) δ ppm: 0.89 (3H, t, J=7 Hz), 0.95 (2H, q, J=7 Hz), 5.43 (2H, s), 5.62 (2H, s), 7.37 (1H, s), 7.8–8.8 (6H, m), 9.10 (1H, s), 11.88 (1H, s)

EXAMPLE 22

Camptothecin-7-aldehyde (40 mg, 0.106 m-mol) was dissolved in a mixture of ethanol (10 ml) and pyridine (1 ml) while warm. Semicarbazide hydrochloride (15 mg, 0.134 m-mol) was added to the solution and the mixture was refluxed for 30 minutes. After allowing the mixture to stand for cooling, the precipitated crystals were collected by filtration, washed with ethanol and dried under reduced pressure whereby 42 mg (91.2%) of camptothecin-7-aldehyde semicarbazone was obtained.

M.P. 280° C. (dec.)

IR$\nu_{max}^{KBr}$ cm$^{-1}$: 3480, 3300, 1740, 1690, 1655, 1585, 1400, 1100, 760

NMR (DMSO-d$_6$) δ ppm: 0.90 (3H, t, J=7 Hz), 1.88 (2H, q, J=7 Hz), 5.43 (2H, s), 5.53 (2H, s), 6.65 (2H, bs), 7.35 (1H, s), 7.8–8.3 (4H, m), 8.86 (1H, s), 10.85 (1H, s)

EXAMPLE 23

Camptothecin-7-aldehyde (200 mg, 0.532 m-mol) was dissolved in ethanol (50 ml) and boron trifluoride-ether (1 ml) was then added to the solution. The mixture was boiled under reflux for 3.5 hours. The reaction mixture was concentrated until dryness under reduced pressure and the residue was shaken with water (100 ml) and chloroform (100 ml). The aqueous phase was extracted with additional chloroform (100 ml). The chloroform layers were combined, dried over magnesium sulfate, filtered and concentrated until dryness under reduced pressure. The residue was purified by way of column chromatography (10% n-hexane-chloroform) on silica gel whereby 209 mg (yield: 87.3%) of 7-diethoxymethylcamptothecin was obtained as yellowish white crystals.

Analytical data of this compound were identical with those shown in Example 10.

EXAMPLE 24

7-Diethoxymethylcamptothecin (250 mg, 0.555 m-mol) was suspended in ice water (15 ml) and conc. hydrochloric acid (25 ml) was added thereto to form a solution. The mixture was stirred for 18 hours at room temperature, diluted with ice water (500 ml) and then extracted with chloroform (200 ml×3). The chloroform layers were dried over magnesium sulfate, filtered and concentrated until dryness under reduced pressure whereby 187 mg (yield: 89.6%) of camptothecin-7-aldehyde was obtained as a yellow solid.

Analytical data of this product were identical with those shown in Example 1.

It is understood that the preceding representative examples may be varied within the scope of the present specification, both as to reactants and reaction conditions, by those skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. A 7-Substituted camptothecin derivative of the formula:

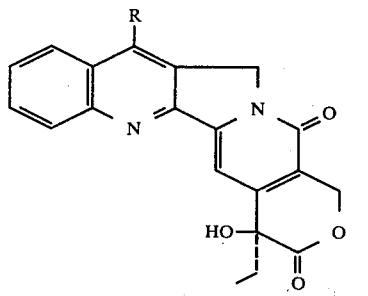

(I)

wherein R represents —CHO, —CH$_2$OR′, —CH(OR′)$_2$ or —CH=N—X where R′ is a lower alkyl group with 1–6 carbon atoms or a phenylalkyl group with 1–3 carbon atoms in the alkylene moiety thereof, and X is a hydroxyl group or —NR$^1$R$^2$ wherein R$^1$ and R$^2$ are the same or different and each represents a hydrogen atom or a lower alkyl group with 1–6 carbon atoms, or when R$^1$ is hydrogen, R$^2$ may be a lower alkyl group with 1–6 carbon atoms, phenyl, a phenyl group substituted by one or more nitro groups, lower alkyl groups or halogen atoms, a carbamoyl group, an acyl group derived from aliphatic carboxylic acids with 1–6 carbon atoms or benzoic acid which may be substituted by a lower alkyl group, alkoxy group, nitro group and/or halogen atoms, isonicotinoyl, a linear or branched aminoalkyl group of 1 to 6 carbon atoms or an amidino group, or when R$^1$ is a lower alkyl group, R$^2$ may be an aminoalkyl group, or when R$^1$ and R$^2$ are each a lower alkyl group they may be combined together to form an alkylene group and may form a 5-membered or 6-membered heterocyclic group together with the nitrogen atom to which R$^1$ and R$^2$ are bound, or non-toxic acid-addition salts or non-toxic alkyl halide quaternary salts thereof.

2. A 7-Substituted camptothecin derivative according to claim 1, wherein R stands for the grouping —CH$_2$OR′ where R′ is a straight or branched chain alkyl group with 1–6 carbon atoms.

3. A 7-Substituted camptothecin derivative according to claim 1, wherein R stands for the grouping —CH(OR′)$_2$ where R′ is a straight or branched chain alkyl group with 1–6 carbon atoms.

4. A 7-Substituted camptothecin derivative according to claim 1, wherein R stands for the grouping —CH$_2$OR′ where R′ is a phenylalkyl group with 1–3 carbon atoms in the alkylene moiety which is linear or branched.

5. A 7-Substituted camptothecin derivative according to claim 1, wherein R stands for the grouping —CH(OR′)$_2$ where R′ is a phenylalkyl group with 1–3 carbon atoms in the alkylene moiety which is linear or branched.

6. Camptothecin-7-aldehyde.

7. Camptothecin-7-aldehyde oxime.

8. Camptothecin-7-aldehyde hydrazone.

9. A 7-Substituted camptothecin derivative according to claim 1, wherein R stands for the grouping —CH=N—X and X for the grouping —NR$^1$R$^2$ where R$^1$ is hydrogen and R$^2$ is a straight or branched chain alkyl group with 1–6 carbon atoms.

10. A 7-Substituted camptothecin derivative according to claim 1, wherein R stands for the grouping —CH=N—X and X for the grouping —NR$^1$R$^2$ where R$^1$ is hydrogen and R$^2$ is a phenyl group unsubstituted or substituted by one or two nitro groups in o- and/or p-position thereof.

11. Camptothecin-7-aldehyde p-toluenesulfonylhydrazone.

12. Camptothecin-7—CH=N—N=C(NH$_2$)$_2$.

13. 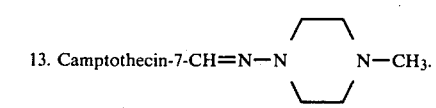

14. Camptothecin-7—CH=N—NH—COCH$_2$N(CH$_3$)$_2$.HCl.

15. Camptothecin-7—CH=N—NH—COCH$_2$N(CH$_3$)$_3$.Cl.

16.

17. 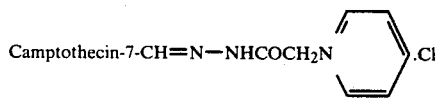
17. 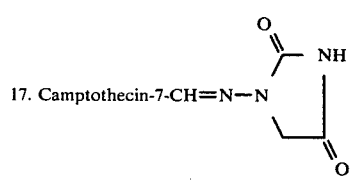
18.
Camptothecin-7-CH=N—NHCO- 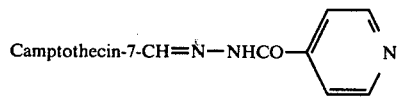
19. Camptothecin-7-aldehyde semicarbazone.
20. Camptothecin-7-aldehyde phenylsemicarbazone.
21. Camptothecin-7-aldehyde thiosemicarbazone.
22.
22. 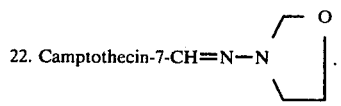
* * * * *